US 8,678,588 B2

(12) United States Patent
Makihira et al.

(10) Patent No.: US 8,678,588 B2
(45) Date of Patent: Mar. 25, 2014

(54) OPTICAL COHERENCE TOMOGRAPHIC IMAGING APPARATUS

(75) Inventors: Tomoyuki Makihira, Kamakura (JP); Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/259,518

(22) PCT Filed: Apr. 15, 2010

(86) PCT No.: PCT/JP2010/057105
§ 371 (c)(1),
(2), (4) Date: Sep. 23, 2011

(87) PCT Pub. No.: WO2010/128626
PCT Pub. Date: Nov. 11, 2010

(65) Prior Publication Data
US 2012/0026463 A1  Feb. 2, 2012

(30) Foreign Application Priority Data

May 8, 2009  (JP) .................................. 2009-113839

(51) Int. Cl.
*A61B 3/14*  (2006.01)
*A61B 3/10*  (2006.01)
(52) U.S. Cl.
CPC ...................................... *A61B 3/102* (2013.01)
USPC ........................................ 351/206; 351/209
(58) Field of Classification Search
USPC ......................................... 351/201–206, 246
See application file for complete search history.

(56) References Cited

U.S. PATENT DOCUMENTS 5,321,501 A  6/1994  Swanson et al.
(Continued)

FOREIGN PATENT DOCUMENTS

DE  102007046507  4/2009
JP  2001-527659  12/2001
(Continued)

OTHER PUBLICATIONS

Pircher et al., Simultaneous SLO/OCT Imaging of the Human Retina with Axial Eye Motion Correction, Optics Express, vol. 15, No. 25, Dec. 10, 2007, pp. 16922-16932.

*Primary Examiner* — Scott J Sugarman
*Assistant Examiner* — Robert E Tallman
(74) *Attorney, Agent, or Firm* — Fitzpatrick, Cella, Harper & Scinto

(57) ABSTRACT

Optical coherence tomographic imaging apparatus creating tomographic image of inspection object includes light splitting means for splitting light from light source into a single reference light and a single sample light, optical path length changing means for changing optical path length of the single reference light, reference light splitting means for splitting the single reference light whose optical path length is changed into a plurality of reference lights, sample light splitting means for splitting the single sample light into a plurality of sample lights, irradiation means for irradiating the inspection object by leading the plurality of sample lights thereto, interference signal forming means for combining returning lights of the plurality of the sample lights from the inspection object irradiated by the irradiation means with the plurality of reference lights passed through the reference-light path, and interference signal obtaining means for obtaining an interference signal from the interference signal forming means.

17 Claims, 5 Drawing Sheets

(56) References Cited

U.S. PATENT DOCUMENTS

| | | |
|---|---|---|
| 7,852,487 B2 | 12/2010 | Rembe et al. |
| 2001/0036002 A1 | 11/2001 | Tearney et al. |
| 2005/0140981 A1 | 6/2005 | Waelti |
| 2008/0284981 A1 | 11/2008 | Fercher et al. |
| 2008/0285049 A1* | 11/2008 | Rembe et al. ............ 356/497 |
| 2010/0284021 A1 | 11/2010 | Hacker |
| 2012/0002214 A1 | 1/2012 | Utsunomiya et al. |

FOREIGN PATENT DOCUMENTS

| | | |
|---|---|---|
| JP | 2008-508068 | 3/2008 |
| JP | 2008-216251 | 9/2008 |
| WO | 98/52021 | 11/1998 |
| WO | 2009/043557 | 4/2009 |

* cited by examiner

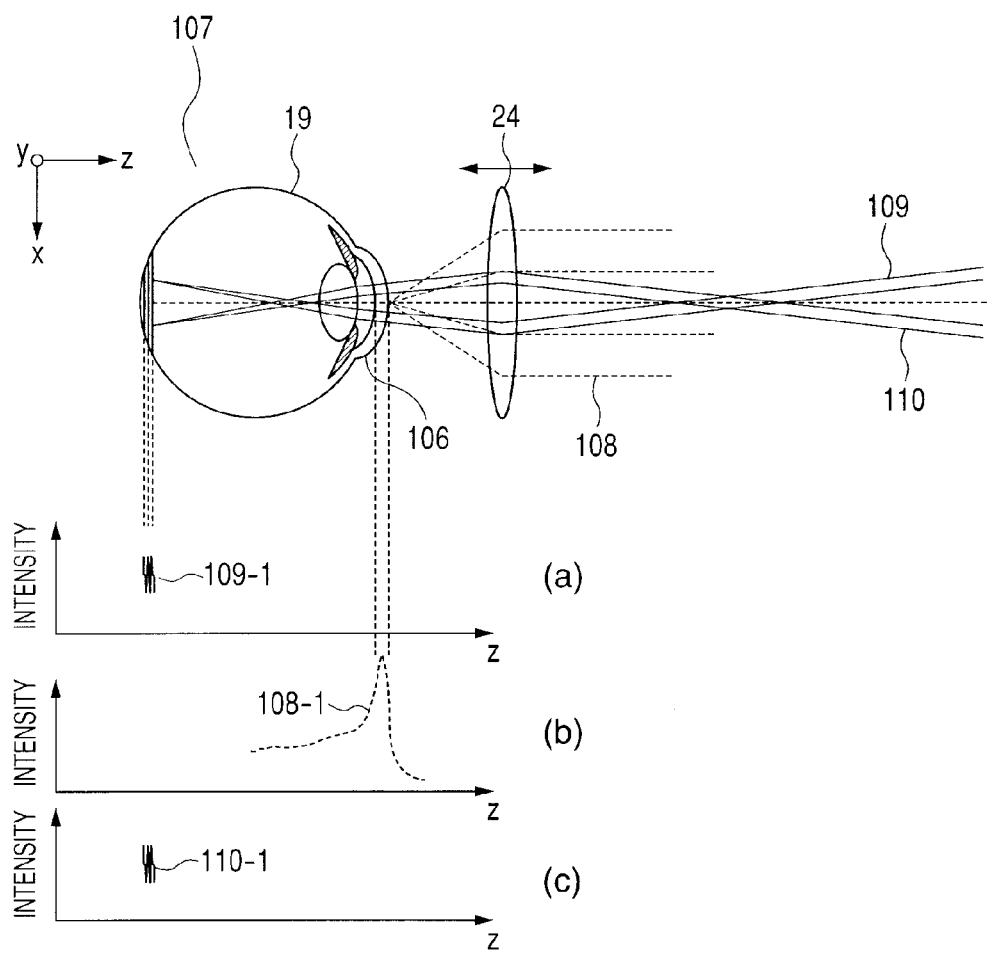

OPTICAL COHERENCE TOMOGRAPHIC IMAGING APPARATUS

TECHNICAL FIELD

The present invention relates to an imaging apparatus based on optical coherence tomography, and more particularly, to an apparatus configuration capable of multi-beam interference processing and apparatus configuration for detecting anteroposterior motion of an eyeball and make corrections for the motion.

BACKGROUND ART

Recently, various optical instruments have come to be used to observe the ocular fundus as an inspection object. For example, an anterior segment imaging device, fundus camera, confocal scanning laser ophthalmoscope, and optical coherence tomographic imaging apparatus (low-coherence, optical coherence tomographic imaging apparatus: hereinafter referred to as an OCT apparatus) are used.

Among others, the OCT apparatus, which allows tomographic images of the ocular fundus to be obtained at high resolution, is currently becoming an indispensable apparatus for specialized retinal outpatient clinics. Also, the OCT apparatus is finding applications in other areas such as the endoscopy area and drawing attention as an apparatus used to obtain arbitrary tomographic images.

The OCT apparatus irradiates the retina with low coherence light, causes scattered light and reflected light, i.e., returning light of the low coherence light, to interfere with reference light and thereby images a layer structure of the retina at high sensitivity. By scanning an inspection object with the low coherence light, the OCT apparatus can obtain tomographic images. In particular, tomographic images of the retina are widely used for ophthalmologic diagnosis.

The OCT apparatus, which is used for diagnosis such as described above, is required to obtain a wide range of tomographic images or high-resolution tomographic images.

Also, to reduce the burden on patients, there is demand to reduce measurement time.

To achieve a reduction in the measurement time, U.S. patent application publication No. 2008/0284981 discloses a multi-beam OCT apparatus which uses a Michelson interferometer for irradiating the retina with multiple beams.

Also, an OCT apparatus for detecting attendant movement of the eyeball is disclosed by M. Pircher et al. (Michael Pircher, Bernhard Baumnn, Erich Gotzinger, Harald Sattmann and Chirstoph K. Hizenberger, "Simultaneous SLO/OCT imaging of the human retina with axial eye motion correction," Optics Express, 10 Dec. 2007, Vol. 15 No. 25 16922-16932).

The reason why such detection is carried out is that the OCT apparatus, which constructs images by scanning, takes relatively much time for imaging and that obtained images are affected by movement of the human eyeball (involuntary eyeball motion known as flicks, i.e., anteroposterior motion of the eyeball together with the entire head).

A technique according to "Simultaneous SLO/OCT imaging of the human retina with axial eye motion correction," Optics Express, 10 Dec. 2007, Vol. 15 No. 25 16922-16932 described above detects anteroposterior corneal position using a low coherence interferometer.

The technique determines amounts of anteroposterior eyeball movement based on detected values of the anteroposterior position, corrects the optical path length of reference light of the low-coherence, optical coherence tomographic imaging apparatus for the amounts of eyeball movement, and thereby reduces anteroposterior deformation of the eyeball in images obtained by the low-coherence, optical coherence tomographic imaging apparatus.

DISCLOSURE OF THE INVENTION

However, the conventional techniques described above have the following problems.

Specifically, the technique disclosed in U.S. patent application publication No. 2008/0284981, which uses multiple beams of reference light, is required to use a large mirror or an increased number of mirrors in a delay line device of optical path length changing means.

Consequently, a stage operating at high speed is loaded with multiple parts or a large part, making it difficult to control the delay line device with high accuracy at high speed.

Also, if an RSOD (Rapid Scanning Optical Ddelay line) or a similar device equipped with lenses is used for the delay line device, the same number of RSODs as lights produced by splitting are needed.

Alternatively, a mirror or lens which receives multiple beams is required.

During observation of the ocular fundus, if there is any anteroposterior movement of the eyeball during a measurement, deformation will occur in the depth direction of obtained images.

The OCT apparatus, which uses low coherence light, provides tomography with high depth resolution.

Also, the depth resolution is improving further due to increases in bandwidth of light sources. Under these circumstances, higher accuracy correction is required in order to prevent deformation in the depth direction.

Also, the technique disclosed in Optics Express, 10 Dec. 2007, Vol. 15 No. 25 is designed to obtain high-quality images by feeding back high-accuracy movement of the eyeball, but requires another independent system of OCT apparatus.

In view of the above problems, an object of the present invention is to provide an optical coherence tomographic imaging apparatus which can reduce deformation of images in the depth direction, reduce measurement time required to obtain high-resolution tomographic images, and reduce increases in the size and number of components.

The present invention provides an optical coherence tomographic imaging apparatus configured as follows.

That is, the present invention provides an optical coherence tomographic imaging apparatus which splits light from a light source into reference light and sample light and creates a tomographic image of an inspection object using interference light obtained by causing returning light of the sample light radiated to the inspection object to interfere with the reference light passing through a reference-light path, including: light splitting means for splitting the light from the light source into a single reference light and a single sample light; optical path length changing means for changing optical path length of the single reference light; reference light splitting means for splitting the single reference light whose optical path length has been changed by the optical path length changing means into a plurality of reference lights; sample light splitting means for splitting the single sample light into a plurality of sample lights; irradiation means for irradiating the inspection object by leading the plurality of sample lights thereto; interference signal forming means for combining returning lights of the plurality of sample lights from the inspection object irradiated by the irradiation means with the plurality of reference lights passed through the reference-light path and thereby form an interference signal; and interference signal obtaining means for obtaining the interference signal from the interference signal forming means.

The present invention can provide an optical coherence tomographic imaging apparatus which can reduce deformation of images in the depth direction, reduce measurement time required to obtain high-resolution tomographic images, and reduce increases in the size and number of components.

Further features of the present invention will become apparent from the following description of exemplary embodiments with reference to the attached drawings.

BRIEF DESCRIPTION OF THE DRAWINGS

FIG. 5 is a simplified diagram for illustrating a configuration used around an eye under examination and a schematic diagram of an obtained image, according to the second embodiment of the present invention.

BEST MODES FOR CARRYING OUT THE INVENTION

The best mode for carrying out the present invention will be described with reference to following embodiments.

Embodiments

First Embodiment

As a first embodiment, a configuration of an optical coherence tomographic imaging apparatus (OCT apparatus) resulting from application of the present invention will be described.

To put it briefly, first, light from an SLD light source is divided into a single reference light and single sample light by a fiber coupler, and optical path length of a reference-light path of the resulting reference light is changed.

After the change, the reference light is split into three lights by reference light splitting means. Also, the sample light is split into three lights—the same number of lights as the reference lights—by the sample light splitting means. Subsequently, each of the sample light is caused to pass through a circulator, led axially symmetrically with respect to the optic axis of an inspection object, i.e., an eye under examination, and directed at a surface to be irradiated, i.e., the retina in the back of the eye, through a collimator and multiple lenses.

Then, after passing through the multiple lenses and collimator, each light reflected by the retina in the back of the eye is received by a spectroscope from the circulator through collimator and the like to transmit a signal which is an output from the spectroscope to a controller which then converts the signal into a tomographic image.

Figure 1:
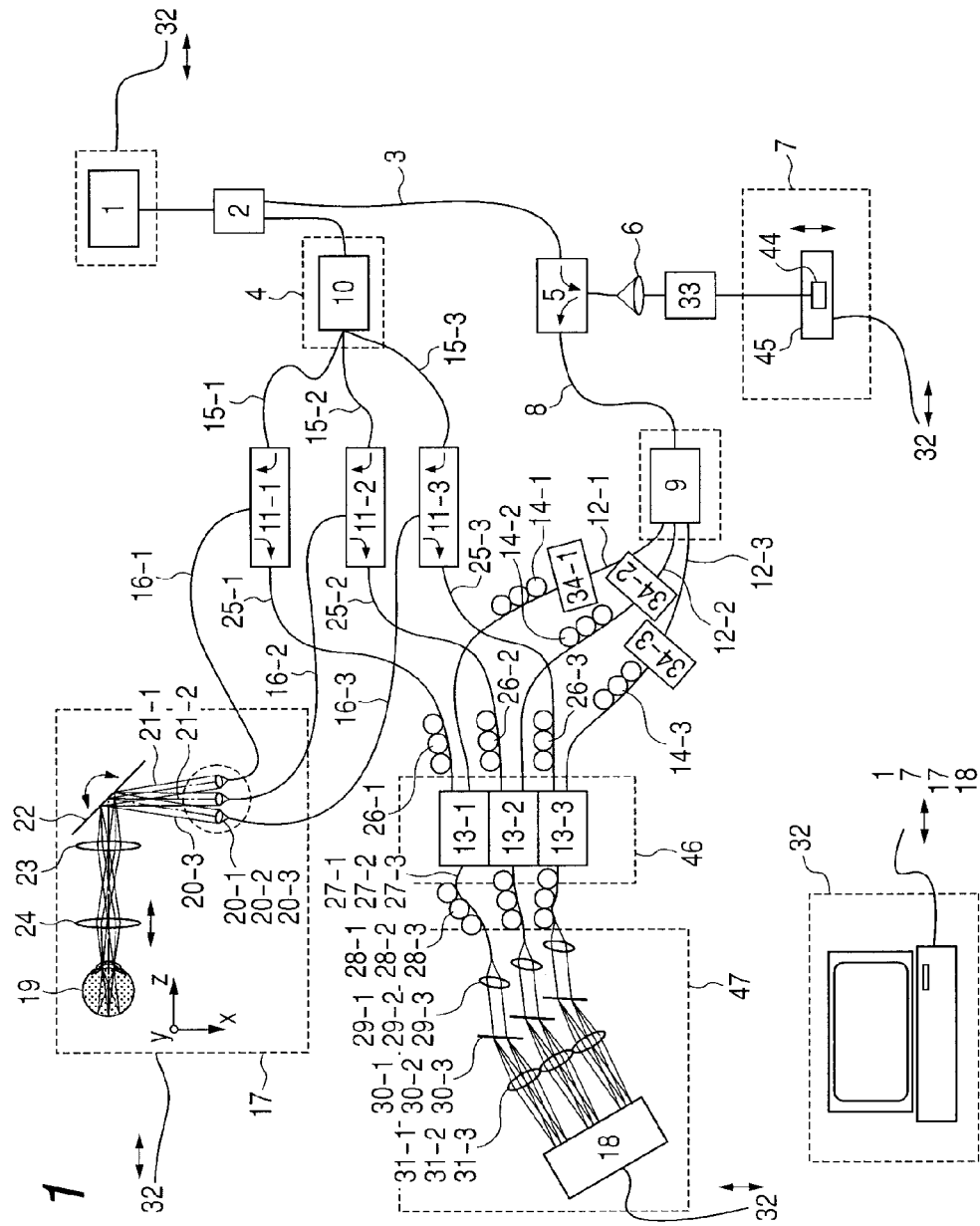
FIG. 1 is a simplified diagram for illustrating a configuration of an optical coherence tomographic imaging apparatus (OCT apparatus) according to a first embodiment of the present invention.

Specifically, as illustrated in FIG. 1, the optical coherence tomographic imaging apparatus according to the present embodiment includes a light source 1, an optical path length changing device 7, optical fiber couplers (light splitting means) 9 and 10, and an equipment configuration 17 used near the retina, an object to be observed.

The optical coherence tomographic imaging apparatus also includes an interference device (interference signal forming means) 46, spectroscopy device (interference signal obtaining means) 47, and a control image analyzer 32.

Next, an overall configuration of high-speed optical coherence tomographic imaging apparatus (OCT apparatus) according to the present embodiment using multiple interference systems will be described concretely, including major devices and optical components.

Light emitted from the light source 1 is separated by an optical fiber coupler 2 into a reference-light optical fiber 3 and sample-light optical fiber 4.

An SLD (Super Luminescent Diode) light source which is a low coherence light source is used as the light source 1. Wavelength of the light source 1 is 840 nm and bandwidth is 50 nm.

The bandwidth is an important parameter related to resolution in the direction of the optical axis of a tomographic image. To improve resolution in the transverse direction of a tomographic image, desirably the wavelength of the light source is short.

The reference light separated by the optical fiber coupler 2 passes through a circulator 5, a collimator 6, and dispersion compensation glass 33 and has its optical path length changed by the optical path length changing device 7 (according to the present embodiment, a voice coil motor stage, hereinafter abbreviated to VCM).

After the optical path length is changed, the reference light is passed through the circulator 5 and an optical fiber 8, and then split into three reference lights by the optical fiber coupler 9.

The split three reference lights are passed through respective fibers 12-1, 12-2, and 12-3 and made to conform to the fundus shape by respective fiber length adjusters 34-1, 34-2, and 34-3. Then, polarization of reference lights is optimized by the respective polarizer's 14-1, 14-2, and 14-3.

Subsequently, the reference lights are led to the interference device 46 in which the reference lights are combined with respective sample lights to form interference lights.

Next, the optical path length changing device 7 which changes the optical path length of the reference light will be described more specifically.

As illustrated in FIG. 1, a light radiated as a parallel light of 1 mm in diameter by the collimator 6 enters the optical path length changing device 7 through the dispersion compensation glass 33.

The optical path length changing device 7 includes a stage 45 and mirror 44, where the stage 45 is driven by the VCM.

According to the present embodiment, the stage equipped with a VCM is used to allow retinal tomographic images to be obtained at high speed.

The VCM can repeat a few μm of travel and stop in directions indicated by arrows in FIG. 1, with high accuracy at high speed.

Although the VCM can drive the stage at high speed, performance of the VCM varies with the weight of components loaded on the stage. Therefore, in order for the VCM to respond quickly, it is necessary to minimize the size of components and decrease the number of components as with the present embodiment.

On the other hand, the sample light is split into three sample lights by the optical fiber coupler 10 and emitted as follows.

The sample lights are passed through respective optical fibers 15-1, 15-2, and 15-3, circulators 11-1, 11-2, and 11-3, and optical fibers 16-1, 16-2, and 16-3, and emitted by respective collimators 20-1, 20-2, and 20-3 as parallel lights.

The parallel lights 21-1, 21-2, and 21-3 are fixed at an irradiation site x-y of the object to be observed, i.e., the eye under examination 19, by an x-y galvanic scanner 22 (y mirror not illustrated) and focused onto the retina of the eye under examination by lenses 23 and 24.

According to the present embodiment, as illustrated in the equipment configuration 17 used near the retina to be observed in FIG. 1, the direction of the optic axis is designated by z, the transverse direction of the eyeball in the fundus plane is designated by x, and the vertical direction is designated by y. The sample lights reach the retina to be observed, through the cornea, crystalline lens, and vitreous body.

The sample lights are transmitted from the respective circulators 11-1, 11-2, and 11-3 to respective optical fibers 25-1, 25-2, and 25-3 through the same optical path as described above by repeating reflections and scattering at various locations.

Then, polarization is optimized by polarizer's 26-1, 26-2, and 26-3, and the sample lights are led to the interference device 46.

According to the present embodiment, the sample lights are converted into parallel lights of 2 mm in diameter by the collimators 20-1, 20-2, and 20-3, and focused onto a desired site on the retina in the back of the eye by the lenses 23 and 24 whose focal lengths are 60 mm and 40 mm, respectively.

The lens 24 is designed to be movable for focus adjustment.

A drivable galvanic mirror, the lenses, and the fiber length adjusters 34-1, 34-2, and 34-3 used to make the sample lights conform to the fundus shape are controlled by the control image analyzer 32.

The reference lights and sample lights described above are caused to interfere with each other by respective optical fiber couplers 13-1, 13-2, and 13-3.

Interference signals are passed through optical fibers 27-1, 27-2, and 27-3, polarizer's 28-1, 28-2, and 28-3, and lens units 29-1, 29-2, and 29-3, and then separated into spectral components for each wavelength by transmission gratings 30-1, 30-2, and 30-3. Then, the reference signals enter a line camera 18 through lenses 31-1, 31-2, and 31-3.

The line camera 18 converts light intensity at each site (wavelength) into a voltage and constructs a tomographic image of the eye under examination 19 using a resulting signal.

According to the present embodiment, the line camera 18 can obtain intensities at 1,024 different wavelengths.

The light source 1 according to the present embodiment has a wide bandwidth and a short spatial coherence length. Consequently, interference fringes can be observed when the reference lights and corresponding sample lights have approximately equal optical path lengths.

Depth direction information about the retina is obtained by converting each interference fringe into a signal on an optical frequency scale and computing the inverse Fourier transform of the signal.

Depth direction information is obtained at each site (x, y) by scanning the retina using the galvanic scanner 22 to obtain a retinal tomographic image of a desired region.

Thus, the line camera 18 provides interference fringes in a spectral region on a wavelength scale.

Next, the interference fringes being information on the wavelength scale are converted into interference fringes on the optical frequency scale for each combination of reference light and sample light by taking characteristics of the line camera 18 and transmission gratings 30 into consideration.

Furthermore, the inverse Fourier transform of the resulting interference fringes on the optical frequency scale is computed to obtain the depth direction information.

In relation to the sample lights, if interference fringes are sensed by driving the x axis of the x-y galvanic scanner 22, interference fringes can be obtained for each x-axis position.

Figure 4:
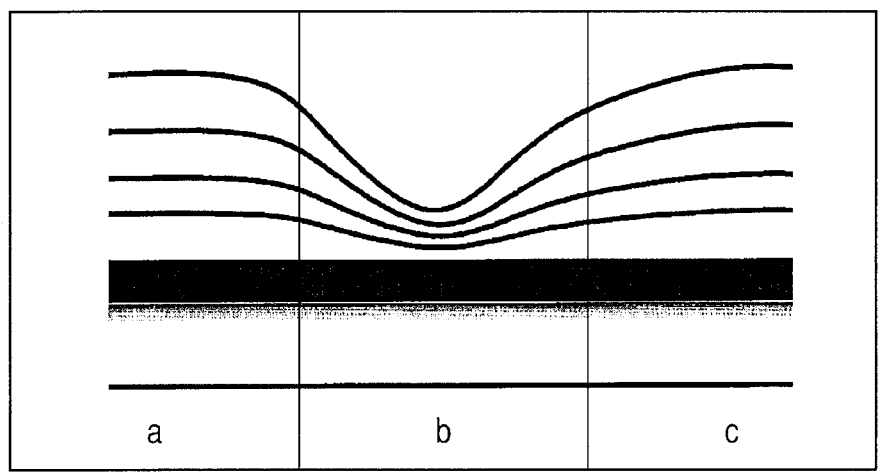
FIG. 4 is a schematic diagram of an image obtained by the OCT apparatus according to the first embodiment of the present invention.

Subsequently, a two-dimensional distribution of returning light intensities on an x-z plane is obtained, providing a tomographic image based on the light intensity distribution as illustrated in FIG. 4.

According to the present embodiment, the intensity distribution from the retina in the back of the eye is received by three collimators arranged in an array (at three locations), and consequently three tomographic images can be obtained simultaneously and successively as exemplified by regions (a), (b), and (c) illustrated in FIG. 4.

Scans may be taken with overlaps for registration of tomographic images.

The present embodiment uses a configuration as described above, but is not limited to such a configuration. Besides, the light source desirably has a low temporal coherence and high spatial coherence, and may be not only a superluminescent diode, but also an ASE (amplified spontaneous emission) light source, femtosecond laser source, or wavelength scanning laser.

Also, the stage used in the optical path length changing means desirably offers accuracy and high-speed scanning, and may be not only a VCM, but also a long-stroke piezo stage.

The optical fiber couplers 9 and 10 may be beam splitters or the like. Also, the interference device 46, line camera 18, and the like may be replaced with other functionally equivalent devices, which provide similar advantages.

Furthermore, the optical path of the interferometer may be made of either a system open to the air or optical fibers.

In detecting anteroposterior position changes of the eye under examination using interference signals, any of a time domain approach, spectral domain approach, and swept-source approach may be used, but the spectral domain approach and swept-source approach are more preferable from the viewpoint of detection speed. Also, although the sample lights after the split are arranged in the x direction, the sample lights may be arranged in the y or z direction.

Also, although in the present embodiment, the reference light and sample light are split into three parts, the present invention provides a similar advantage when applied to a system in which the reference light and sample light are split into larger number of parts to speed up the apparatus. As with the present embodiment, when optical path length changing means serving as a delay line is installed between the means for splitting a light into a reference light and sample light and the means for splitting the reference light into multiple parts, the configuration of the optical path length changing means can be minimized.

Consequently, interference between multiple beams can be caused using a simple configuration and a speedup can be achieved.

Second Embodiment

In a second embodiment, an exemplary configuration designed to provide high-resolution retinal tomographic images will be described, where the high-resolution retinal tomographic images are obtained through feedback control which involves feeding back detected movements of an eyeball in a z-axis direction to an OCT delay line.

According to the present embodiment, as with the first embodiment, out of multiple sample lights possessed by an optical coherence tomographic imaging apparatus, an arbitrary sample light is focused onto the cornea in the anterior segment of the eye and anteroposterior movement of the eyeball is measured.

By feeding back the measurement results to the delay line, high-quality retinal tomographic images can be obtained without being influenced by the movement of the eyeball.

Figure 2:
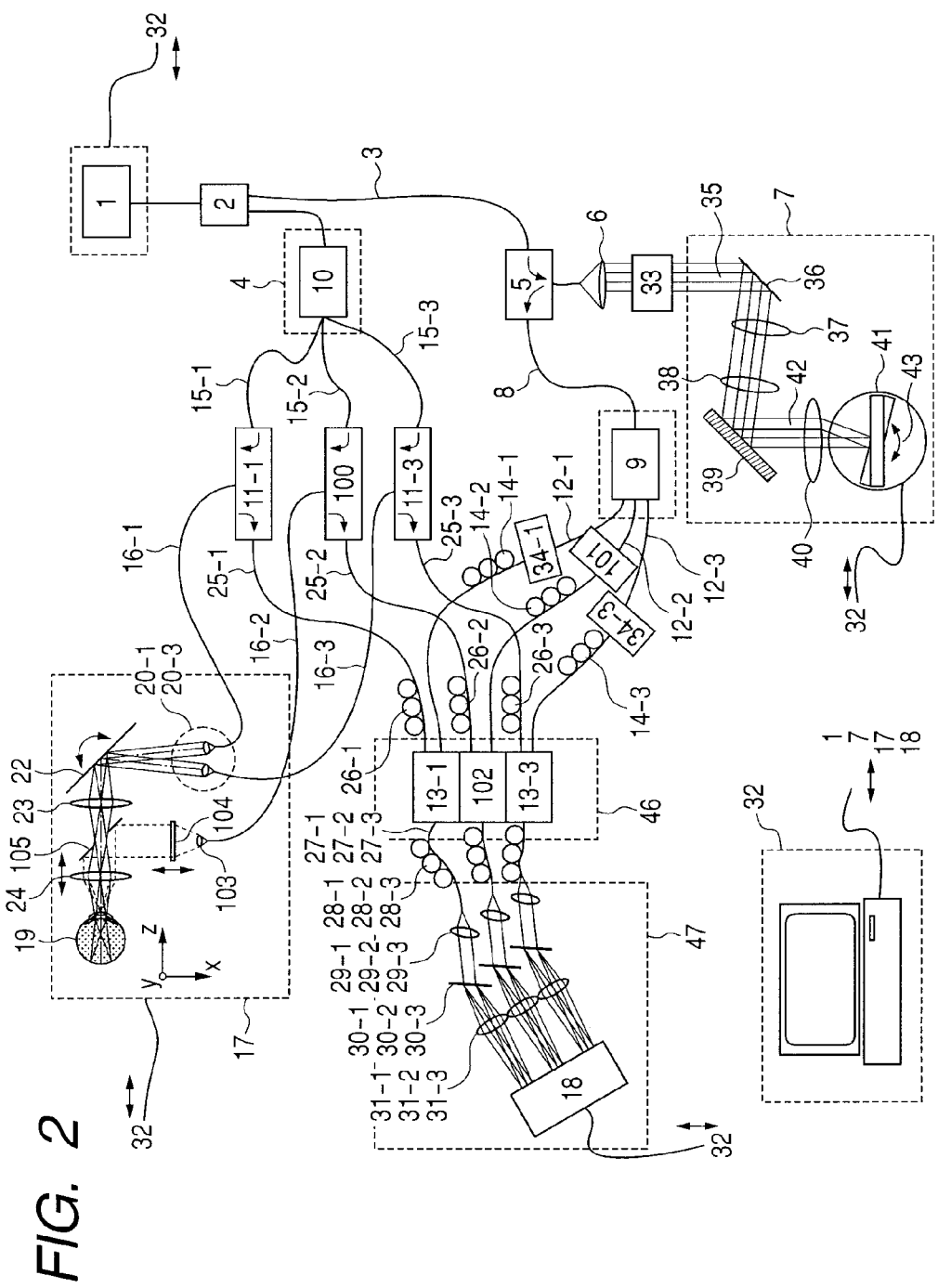
FIG. 2 is a simplified diagram for illustrating a configuration of the optical coherence tomographic imaging apparatus (OCT apparatus) according to the first embodiment of the present invention.
Figure 3:
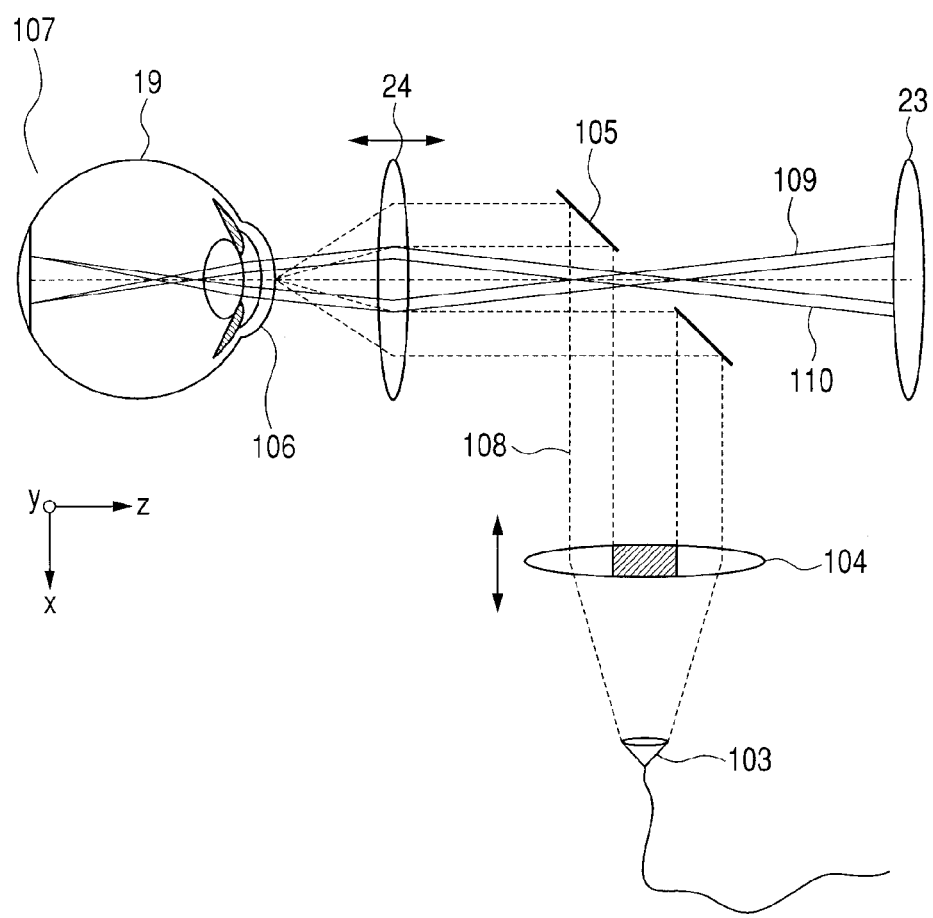
FIG. 3 is a simplified diagram for illustrating a configuration used around an eye under examination according to a second embodiment of the present invention.

FIG. 2 is a diagram illustrating principal parts of the optical coherence tomographic imaging apparatus (OCT apparatus) according to the present embodiment. FIG. 3 is a diagram illustrating an equipment configuration used near the eyeball to be observed.

A light source, light splitting means, a spectroscope, and a data construction method of the OCT apparatus according to the present embodiment are the same as the first embodiment, and thus description thereof will be omitted.

As illustrated in FIG. 2, the present embodiment differs greatly from the first embodiment in optical path length changing means, the equipment configuration used near the eyeball to be observed, and an interference device.

First, the optical path length changing device 7 illustrated in FIG. 2 will be described.

According to the present embodiment, in order to respond to eyeball motion, a delay line device running at high speed is required. Therefore, an RSOD (rapid scanning optical delay line) is used as the optical path length changing device.

A concrete configuration of such an RSOD is disclosed, for example, in Japanese Patent Application Laid-Open No. 2001-527659 (National Publication of International Patent Application). Being equipped with a diffraction grating and mirror, the RSOD can change optical path length by swinging the mirror with a scanner and thereby achieve a speedup.

With this RSOD, even if the direction of an optical axis changes during reflection as the mirror is swung, the optical axis can be adjusted by the diffraction grating, whose angle during transmission or reflection is designed to be determined by incident wavelength.

Light emitted as a parallel light of 1 mm in diameter by the collimator 6 enters the optical path length changing device 7 (RSOD) through the dispersion compensation glass 33.

The RSOD 7 includes a reflecting mirror 36 for an incident light 35, lenses 37 and 38, a diffraction grating 39 with a grid spacing (d), and a lens 40.

A mirror 41 is located a distance approximately equal to the focal length (f) away from the lens 40, and the diffraction grating 39 disperses a spectrum of the incident light 35.

When the mirror 41 is tilted as indicated by a broken line in FIG. 2, the light returns to the collimator 6 as indicated by broken lines 42, resulting in a change in the optical path length of reference light.

In FIG. 2, position of the mirror 41 after reflection is illustrated as being shifted greatly, for the sake of simplicity. An angle of the mirror 41 can be changed via a rotating member 43 whose rotation can be controlled.

The mirror is controlled by the control image analyzer 32.

Although a multipath mirror is not used for the RSOD in the present embodiment, if a multipath mirror is used for the RSOD and light is returned to the collimator 6 with reduced losses by changing the optical path length, the optical path length can be controlled more accurately.

Next, a position detecting optical system for the anterior segment of the eye will be described.

Out of the three sample lights resulting from the split done by the light splitting means 10, the light along the fiber 15-2 is led to a collimator 103 via a circulator 100. As illustrated in FIG. 3, the light is converted into a hollow parallel light 108 with a diameter of 5 mm by a collimator 103 and movable annular lens 104.

Furthermore, the light is passed through an aperture mirror 105 and focused by a movable lens 24 onto the eyeball's cornea 106.

The annular lens 104 and the lens 24 are drivable lenses and controlled by the control image analyzer 32.

Returning light such as scattering and reflections from the eyeball's cornea 106 follows the same path.

After returning from the collimator 103 to the circulator 100, light from the fiber 25-2 is polarized and optimized by the polarizer 26-2 and interference is caused by an interference system (interference signal forming means) 102. Then, the light is received by the spectroscopy device (interference signal obtaining means) 47 as in the case of the first embodiment.

The signal detected by the spectroscopy device (interference signal obtaining means) 47 goes through FFT signal processing, and cornea position is detected.

This configuration allows the cornea to be brought into focus independently of parallel lights 109 and 110, and the corneal apex to be brought into focus during scanning as well.

Next, as an example of correction means, means for controlling the optical path length changing means based on information detected by motion detecting means will be described, where the motion detecting means detects movement of the inspection object, i.e., the eyeball.

FIG. 5 conceptually illustrates the cornea's shape and an interference signal.

In the conceptual diagram of an output signal in FIG. 5, as in the case of FIG. 3, data indicated by 108-1 in a center graph (b) is obtained when the parallel light 108 is focused on the cornea.

The abscissa represents the z-axis direction (depth direction) and the ordinate represents interference signal intensity.

A signal of a reflection component in a corneal area appears as a peak, as shown in 108-1 in FIG. 5. Displacement of the peak in 108-1 is sensed and an amount by which the mirror is driven is controlled based on the amount of displacement.

Specifically, when the eyeball is displaced in the anteroposterior direction, the peak position in 108-1 moves in the left-right direction (z-axis direction). In so doing, if the eyeball is displaced forward, the peak position is displaced rightward. If the eyeball is displaced backward, the peak position is displaced leftward.

A target peak position is specified in advance and value of the mirror 41 in the RSOD is determined and controlled based on the amount of displacement from the target peak position, i.e., deviation.

Next, the control will be described.

The sample lights 109 and 110, which are parallel lights, are focused on the retina by controlling the RSOD device 7 and lens 24.

Next, the parallel light 108 is focused on the cornea 106 by controlling the annular lens 104.

When the controller can detect feature points on the retina and cornea successfully, OCT images are obtained.

If the controller fails to detect feature points, focusing and positioning are carried out again. The feature points may be obtained at sites where they are easy to detect, such as at the yellow spot or corneal apex.

When obtaining the OCT images, OCT images of the retina are obtained by monitoring the corneal apex at a frequency of 10 kHz, converging the amount of displacement from the initial position of the feature point, and feeding back the amount of displacement to the RSOD.

Thus, the OCT apparatus which achieves a speedup by obtaining OCT images simultaneously using multiple sample lights uses an arbitrary sample light to detect eyeball motion.

This enables implementing an optical coherence tomographic imaging apparatus which can obtain high-quality OCT images at high speed, without the need for new components.

Although the present embodiment uses an SLD light source 1 with a wavelength of 840 nm and a bandwidth of 50 nm as in the case of the first embodiment, similar advantages can be obtained using other bandwidths.

Also, although the tomography apparatus uses two sample lights to obtain tomographic images of the retina and uses one sample light to detect eyeball motion, similar advantages can be obtained using a larger number of sample lights.

Also, advantages similar to those of the present embodiment can also be obtained in another embodiment by using a dichroic mirror, beam splitter, and the like instead of fibers in the optical system used near the eyeball to be observed, the optical path splitting means, and the interference system.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-113839, filed May 8, 2009, which is hereby incorporated by reference herein in its entirety.

The invention claimed is:

1. An optical coherence tomographic imaging apparatus comprising:
light splitting unit configured to split light from a light source into a single reference light and a single sample light;
optical path length changing unit configured to change an optical path length of the single reference light;
reference light splitting unit configured to split the single reference light whose optical path length has been changed by the optical path length changing unit into a plurality of reference lights;
sample light splitting unit configured to split the single sample light into a plurality of sample lights;
irradiation unit configured to irradiate an inspection object by leading the plurality of sample lights thereto;
light combining unit configured to generate a plurality of interference lights which are returning lights of the plurality of the sample lights from the object irradiated by the irradiation unit combined with the plurality of reference lights.

2. The optical coherence tomographic imaging apparatus according to claim 1, further comprising:
a motion detecting unit configured to detect movement of the inspection object based on at least one of the plurality of interference lights; and
a control unit configured to control the optical path length changing unit based on the detected movement.

3. The optical coherence tomographic imaging apparatus according to claim 2, wherein at least one of the plurality of sample lights is directed to a site on the inspection object different from that of other sample lights of the plurality of sample lights.

4. The optical coherence tomographic imaging apparatus according to claim 1, wherein the optical path length changing unit is configured with a rapid scanning optical delay line.

5. The optical coherence tomographic imaging apparatus according to claim 1, wherein the inspection object is an eye, further comprising a scanning unit configured to scan the plurality of the sample lights to the back of the eye,
wherein the plurality of the sample lights irradiates at the anterior segment of the eye by the irradiation unit as parallel lights and are led to a back of the eye as a state focused onto the back of the eye.

6. The optical coherence tomographic imaging apparatus according to claim 1, wherein the inspection object is an eye, further comprising a tomographic image acquiring unit for acquiring a tomographic image of the back of the eye in accordance with the plurality of interference lights.

7. The optical coherence tomographic imaging apparatus according to claim 6, wherein the plurality of the sample lights radiated to the inspection object by the irradiation means are led axially symmetrically with respect to an optic axis of the eye.

8. The optical coherence tomographic imaging apparatus according to claim 2, wherein the inspection object is an eye, and the motion detecting unit detects the movement of the eye in the direction of an optical axis based on the interference signal of the anterior of the eye.

9. The optical coherence tomographic imaging apparatus according to claim 8, wherein the motion detecting unit which detects the anteroposterior movement of the eye detects anteroposterior movement of the cornea of the eye.

10. The optical coherence tomographic imaging apparatus according to claim 1, further comprising a plurality of adjusting units configured to adjust optical path length differences between the plurality of the reference lights and the plurality of the sample lights.

11. The optical coherence tomographic imaging apparatus according to claim 10, wherein the inspection object is an eye, and the optical coherence tomographic imaging apparatus contains a controlling unit configured to control the plurality of adjusting units in accordance with the shape of the eye.

12. The optical coherence tomographic imaging apparatus according to claim 10, wherein the plurality of adjusting units are the plurality of fiber length adjusting units for changing each fiber length of the optical paths of the plurality of the reference lights.

13. The optical coherence tomographic imaging apparatus according to claim 1, wherein the optical path length changing unit is disposed in an optical path of the single reference light, and comprises a reflecting member and a unit for rotation-controlling the reflecting member.

14. The optical coherence tomographic imaging apparatus according to claim 13, wherein the optical path length changing unit comprises a diffraction grating for dispersing spectrum of the single reference light, and the reflecting member reflects the light from the diffraction grating.

15. The optical coherence tomographic imaging apparatus according to claim 1, further comprising a dispersion compensation unit disposed in an optical path of the single reference light,
wherein the optical path length changing unit comprises a reflection member for reflecting a light from the dispersion compensation unit.

16. An optical coherence tomographic imaging method comprising:
a light splitting step of splitting light from a light source into a single reference light and a single sample light;

an optical path length changing step of changing an optical path length of the single reference light;

a reference light splitting step of splitting the single reference light whose optical path length has been changed in the optical path length changing step into a plurality of reference lights;

a sample light splitting step of splitting the single sample light into a plurality of sample lights;

an irradiation step of irradiating an inspection object by leading the plurality of sample lights thereto;

a light combining step of generating a plurality of interference lights which are returning lights of the plurality of the sample lights from the object irradiated in the irradiation step combined with the plurality of reference lights.

17. A non-transitory medium storing computer program code for instructing a computer to perform an optical coherence tomographic imaging method comprising:

a light splitting step of splitting light from a light source into a single reference light and a single sample light;

an optical path length changing step of changing an optical path length of the single reference light;

a reference light splitting step of splitting the single reference light whose optical path length has been changed in the optical path length changing step into a plurality of reference lights;

a sample light splitting step of splitting the single sample light into a plurality of sample lights;

an irradiation step of irradiating an inspection object by leading the plurality of sample lights thereto;

a light combining step of generating a plurality of interference lights which are returning lights of the plurality of the sample lights from the object irradiated in the irradiation step combined with the plurality of reference lights.

* * * * *